(12) United States Patent
Kuwabara et al.

(10) Patent No.: US 9,073,938 B2
(45) Date of Patent: Jul. 7, 2015

(54) METHOD FOR PRODUCING AROMATIC COMPOUND

(75) Inventors: Hirokazu Kuwabara, Tokyo (JP); Masaaki Ikeda, Tokyo (JP); Kazuo Takimiya, Higashihiroshima (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 271 days.

(21) Appl. No.: 12/451,537

(22) PCT Filed: May 13, 2008

(86) PCT No.: PCT/JP2008/058764
§ 371 (c)(1),
(2), (4) Date: Nov. 17, 2009

(87) PCT Pub. No.: WO2008/146597
PCT Pub. Date: Dec. 4, 2008

(65) Prior Publication Data
US 2010/0137617 A1    Jun. 3, 2010

(30) Foreign Application Priority Data
May 24, 2007    (JP) .................................. 2007-138028

(51) Int. Cl.
*C07D 495/04* (2006.01)
*C07D 495/22* (2006.01)
*C07D 517/04* (2006.01)

(52) U.S. Cl.
CPC ............ *C07D 495/04* (2013.01); *C07D 495/22* (2013.01); *C07D 517/04* (2013.01)

(58) Field of Classification Search
CPC .................................................... C07D 495/04
See application file for complete search history.

(56) References Cited

U.S. PATENT DOCUMENTS

| | | | |
|---|---|---|---|
| 3,663,568 A | 5/1972 | Roos et al. | |
| 2005/0193504 A1* | 9/2005 | Glenn et al. | 8/405 |
| 2005/0258398 A1* | 11/2005 | Kobayashi et al. | 252/299.61 |

FOREIGN PATENT DOCUMENTS

| | | | | |
|---|---|---|---|---|
| EP | 1357163 A1 | 10/2003 | | |
| EP | 1378513 A1 | 1/2004 | | |
| EP | 2147923 A1 | 1/2010 | | |
| JP | 6-177380 A | 6/1994 | | |
| JP | 10340786 A | * 12/1998 | ............ | H05B 33/14 |
| JP | 2001-94107 A | 4/2001 | | |
| JP | 2002-265473 A | 9/2002 | | |
| JP | 2005-154371 | 6/2005 | | |
| JP | 2005-330185 A | 12/2005 | | |
| JP | 2007-145833 | 6/2007 | | |

OTHER PUBLICATIONS

Vafai et. al. Bulletin des Societes Chimiques Belges, 1966, 75(3-4), 145-56 (abstract only).*

Takimiya, "Molecular modification of 2,6-diphenylbenzo[1,2-b:4,5-b']dichalcogenophenes by introduction of strong electron-withdrawing groups: conversion from p- to n-channel OFET materials." Chemistry Letters, 2006 35(10), 1200-1201.*
European Communication dated Jul. 11, 2011 in corresponding foreign patent application No. EP 08752644.8.
European communication, dated Dec. 22, 2010, in corresponding foreign application EP 08 75 2644.
Kurita et al, "Synthesis of 1-Benzometalloles Containing Group 14, 15, and 16 Heavier Elements via a Common Dilithiostyrene Intermediate", Chemical and Pharmaceutical Bulletin, vol. 42, No. 7, 1994, pp. 1437-1441—XP002611740.
Muth et al, "The Preparation of 2-Methylthianaphtalene and 2-Methylselenonaphtalene and Their Ultraviolet Absorption Spectra", Journal of Organic Chemistry, vol. 21, 1956, pp. 576-578, XP002611741.
Hansck et al, "Synthesis of 6-Substituted Thianaphtenes", Journal of Organic Chemistry, vol. 20, No. 8, 1955, pp. 1056-1061, XP002611742.
Broggini et al, "Efficient approach to the unknown isoxazolo[3,4-d]pyrid ine ysytem by regioselective intramolecular nitrone cycloadditions", Tetrahedron, vol. 61, No. 14, Apr. 4, 2005, pp. 3525-3531, XP025383205.
Martin-Smith et al, "Bromination Studies with 5-Hydroxybenziothiophene", Journal of the American Chemical Society, vol. 78, 1956, pp. 6177-6179, XP002611743.
A. Fredga, "Steric Correlations by the Quasi-Racemate Method", Tetrahedron, vol. 8, 1960, pp. 126-144, XP002611744.

(Continued)

*Primary Examiner* — David K O Dell
(74) *Attorney, Agent, or Firm* — Nields, Lemack & Frame, LLC

(57) ABSTRACT

Disclosed is a method for producing an aromatic compound represented by the general formula (2) below, which is characterized in that a compound represented by the general formula (1) below is reacted with a sulfur compound (at least one member selected from the group consisting of sulfur, hydrogen sulfide, metal hydrosulfides and metal sulfides) or a selenium compound. (In the formula (1), $R^1$ represents a hydrogen atom, a halogen atom, a hydroxyl group, a cyano group, a nitro group, an ester group, an optionally substituted alkyl group having 1-18 carbon atoms or the like; $R^2$ represents a halogen atom; $R^3$ represents a hydrogen atom, C≡C—$R^1$ or $R^2$; and n represents an integer of 0-4. When n is not less than 2, $R^3$'s may be the same as or different from each other.) (In the formula (2), $R^1$, $R^3$ and n are as defined in the formula (1); and X represents a sulfur atom or a selenium atom.)

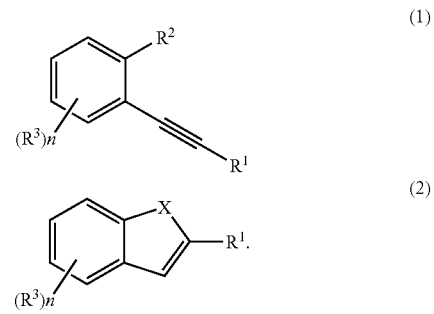

1 Claim, No Drawings

(56) References Cited

OTHER PUBLICATIONS

Savel'ev et al, "New Methods for the Synthesis of Amides of Benzo[b]thiophene-2-Carboxylic Acid", Chemistry of Heterocyclic Compounds, vol. 14, 1978, pp. 1085-1087, XP002611745.

European Communication dated Jul. 11, 2011 in corresponding foreign patent application No. EP 11167229.1.

International Search Report dated Jul. 15, 2008.

Synthetic Communications, 28(4), 713-727 (1998); Haruki Sashida et al.; "A Convenient One-Pot Preparation of Benzo[b]-Tellurophenes,—Selenophenes, and—Thiophenes from o-Bromoethynylbenzenes".

J.Am.Chem. Soc. 2004, 126, 5084-5085; Kazuo Takimiya et al.; "2,6-Diphenylbenzo[1,2-b:4,5-b']dichalcogenophenes: A New Class of High-Performance Semiconductors for Organic Field-Effect Transistors".

Organic Letters 2004, vol. 6, No. 2, 273-276; Yohann Nicolas et al.; "Planarized Star-Shaped Oligothiophenes with Enhanced p-Electron Delocalization".

Synthesis 2004, No. 13, pp. 2131-2134; Irena D. Ivanchikova et al.; "A Simple Synthesis of Angular Anthrathiophenediones via Acetylenic Derivatives of Anthraquinone".

ARKTVOC 2003 (xiii) 87-100; Mark S. Shvartsberg et al.; "Synthesis of sulfur-containing heterocyclic compounds by cyclocondensation of acetylenic derivatives of anthraquinone with sodium sulfide".

J.Org. Chem. 2005, 70, 10569-10571; Kazuo Takimiya et al.; "Facile Synthesis, Structure, and Properties of Benzo[1,2-b:4,5-b']dichalcogenophenes".

Organic Letters 2001, vol. 3, No. 5, 651-654; Bernard L. Flynn et al.; "A Novel Palladium-Mediated Coupling Approach to 2,3-Disubstituted Benzo[b]thiophenes and Its Application to the Synthesis of Tubulin Binding Agents".

Supporting Information, pp. S1-S17, related to Organic Letters, 2004, vol. 6, No. 2, pp. 273-276, "Planarized Starshaped Oligothiophenes with Enhanced Pi-Electron Delocalization", Nicolas, et al.

Japanese communication, with English translation, mailed Jun. 10, 2014 in corresponding Japanese patent application No. JP 2013-83052.

* cited by examiner

METHOD FOR PRODUCING AROMATIC COMPOUND

TECHNICAL FIELD

The present invention relates to a method for producing an aromatic compound. More specifically, the present invention relates to production of a benzochalcogenophene derivative.

BACKGROUND ART

Conventionally, several methods have been known for producing a benzochalcogenophene derivative.

For example, NON-PATENT DOCUMENTS 1 and 2 disclose a method for synthesizing a benzochalcogenophene derivative by reacting sodium sulfide with a 2-halogeno-1-acetylene derivative in ethanol.

NON-PATENT DOCUMENT 3 discloses a method for synthesizing [1]benzochalcogeno[3,2-b][1]benzochalcogenophene by reacting tert-butyllithium with bis(2-bromophenyl)acetylene at low temperature in THF (tetrahydrofuran) solvent, followed by addition of sulfur, selenium, or tellurium. However, problems of operational safety and extreme difficulty in industrial application exist because tert-butyllithium ignites when reacted with water in the air.

NON-PATENT DOCUMENT 4 discloses a method for synthesizing a benzothiophene derivative characterized by reacting butyllithium with a 2-bromo-acetylene derivative. However, questions of operational safety and industrial application are similarly raised because alkyllithium is used in this method. Accordingly, establishment of a safer and industrially applicable method for producing the compound has been demanded.

NON-PATENT DOCUMENT 5 discloses a method for producing a trithienobenzene derivative from dibromothiophene through three steps. However, the current reality is that the above method is far from a safe industrial production method because raw materials are expensive, and further, butyllithium is used in two steps and reacted at ultra-low temperature.

NON-PATENT DOCUMENT 1: Synthesis, (13), 2131-2134 (2004)
NON-PATENT DOCUMENT 2: ARKIVOC (Gainesville, Fla., United States), (13), 87-100 (2003)
NON-PATENT DOCUMENT 3: Journal of Organic Chemistry 70(25), 10569-10571 (2005)
NON-PATENT DOCUMENT 4: Organic Letters, 3(5), 651-654 (2001)
NON-PATENT DOCUMENT 5: Organic Letters, 6(2), 273-276 (2004)

DISCLOSURE OF THE INVENTION

Problems to be Solved by the Invention

The present invention relates to a simple and efficient method for producing an aromatic compound. More particularly, an object of the present invention is to provide an industrially applicable method for producing a benzochalcogenophene derivative represented by the following formula (2) in a simple and efficient manner.

Means for Solving the Problems

The present inventors conducted extensive and thorough research to solve the aforementioned problems. As a result, the inventors completed the present invention by finding that a compound represented by the following formula (2) is simply and efficiently produced by reacting a 2-halogeno-1-acetylene derivative represented by a general formula (1) with a sulfur compound or a selenium compound.

Namely, the present invention provides the followings;

(1) A method for producing a compound represented by the following formula (2), comprising reacting a compound represented by the following formula (1) with at least one sulfur compound selected from the group consisting of sulfur, hydrogen sulfide, metal hydrosulfide, and metal sulfide or a selenium compound;

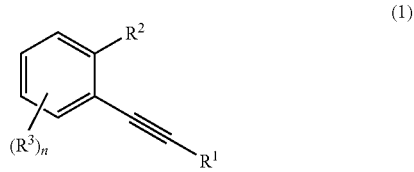

(1)

wherein, $R^1$ represents a hydrogen atom, a halogen atom, a hydroxyl group, a cyano group, a nitro group, a carboxyl group, a formyl group, an ester group, a substituted or unsubstituted C1-C18 alkyl group, a substituted or unsubstituted aryl group, a substituted or unsubstituted heteroaryl group, a substituted or unsubstituted C1-C18 alkoxyl group, a substituted or unsubstituted amino group, a silyl group substituted with C1-C18 alkyl, or a substituted or unsubstituted C2-C19 acyl group; $R^2$ represents a halogen atom; $R^3$ represents a hydrogen atom, C≡C—$R^1$, $R^1$, or $R^2$; and n represents an integer of 0 to 4, and wherein when n is 2 or greater, plural $R^3$s can be identical or different from each other, and when n is 2 and $R^3$s are substituted at adjacent carbon atoms forming the benzene ring represented by the formula (1), the $R^3$s can be bonded together to form a benzene ring;

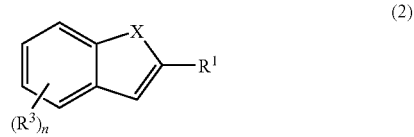

(2)

wherein, $R^1$, $R^3$, and n have the same meanings as in the above formula (1), and X denotes a sulfur atom or a selenium atom.

(2) The method according to the above (1), wherein the halogen atom represented by $R^2$ is a bromine atom or an iodine atom.

(3) The method according to the above (1) or (2), wherein the sulfur compound is sodium sulfide or sodium hydrosulfide.

(4) The method according to any one of the above (1) to (3), wherein a reaction mixture contains at least one solvent having a boiling point of 100° C. or higher.

(5) The method according to the above (4), wherein the solvent having a boiling point of 100° C. or greater is amide, glycol, or sulfoxide.

(6) The method according to the above (5), wherein the amide is a solvent selected from N-methyl-2-pyrrolidone, N,N-dimethylformamide, and N,N-dimethylacetamide; the glycol is a solvent selected from ethylene glycol, propylene glycol, and polyethylene glycol; and the sulfoxide is dimethyl sulfoxide.

(7) The method according to the above (6), wherein the reaction is carried out in the presence of at least one metal catalyst selected from the group consisting of copper, copper (I) chloride, copper(II) chloride, copper(I) bromide, copper (II) bromide, copper(I) iodide, and copper(II) iodide.

(8) The method according to any one of the above (1) to (7), wherein the compound represented by the formula (1) is a compound represented by any one of the following formulas (3), (4), and (5);

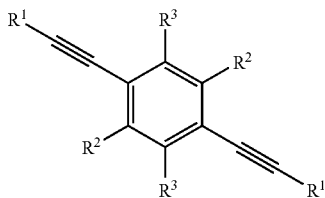

(3)

wherein, $R^1$, $R^2$, and $R^3$ have the same meanings as in the formula (1);

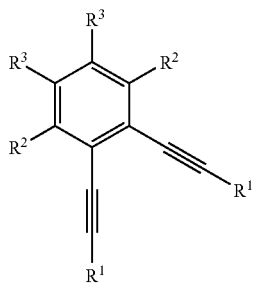

(4)

wherein, $R^1$, $R^2$, and $R^3$ have the same meanings as in the formula (1);

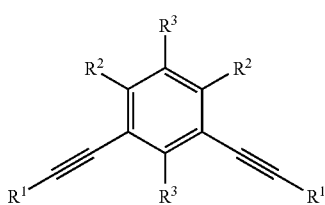

(5)

wherein, $R^1$, $R^2$, and $R^3$ have the same meanings as in the formula (1).

(9) The method according to any one of the above (1) to (8), wherein the compound represented by the formula (1) is a compound represented by the following formula (6);

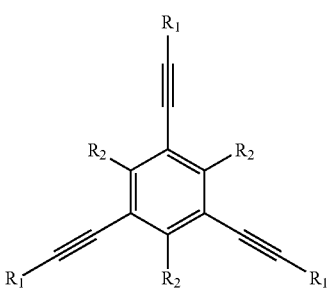

(6)

wherein, $R^1$ and $R^2$ have the same meanings as in the formula (1).

(10) The method according to the above (9), wherein the halogen atom represented by $R^2$ is a bromine atom or a chlorine atom.

(11) A compound represented by the formula (2), which is produced by the method according to any one of the above (1) to (10).

Advantages of the Invention

The present invention enabled industrially applicable production of a benzochalcogenophene derivative represented by the above formula (2) in a simple and efficient manner.

BEST MODE FOR CARRYING OUT THE INVENTION

The production method of the present invention is described in detail hereinbelow.

The present invention relates to a method for producing the compound represented by the above formula (2), characterized by reacting the compound represented by the above formula (1) with at least one sulfur compound selected from the group consisting of sulfur, hydrogen sulfide, metal hydrosulfide, and metal sulfide, or a selenium compound.

For the formula (1), $R^1$ represents a hydrogen atom, a halogen atom, a hydroxyl group, a cyano group, a nitro group, a carboxyl group, a formyl group, an ester group, a substituted or unsubstituted C1-C18 alkyl group, a substituted or unsubstituted aryl group, a substituted or unsubstituted heteroaryl group, a substituted or unsubstituted C1-C18 alkoxyl group, a substituted or unsubstituted amino group, a C1-C18 alkyl group substituted with a silyl group, or a substituted or unsubstituted C2-C19 acyl group. $R^2$ represents a halogen atom. $R^3$ represents a hydrogen atom, C≡C—$R^1$, or R2. A letter n represents an integer of 0 to 4. When n is 2 or greater, plural $R^3$s can be identical or different from each other.

Preferably, the above $R^1$ is a hydrogen atom, a halogen atom, a cyano group, a substituted or unsubstituted C1-C18 alkyl group, a substituted or unsubstituted aryl group, a substituted or unsubstituted heteroaryl group, a substituted or unsubstituted C1-C18 alkoxyl group, a substituted or unsubstituted amino group, a C1-C18 alkyl group substituted with a silyl group, and a substituted or unsubstituted C2-C19 acyl group. More preferably, $R^1$ is a hydrogen atom, a halogen atom, a cyano group, an unsubstituted C1-C18 alkyl group, a substituted or unsubstituted aryl group, a substituted or unsubstituted heteroaryl group, an unsubstituted C1-C18 alkoxyl group, an unsubstituted amino group, a C1-C18 alkyl group substituted with a silyl group, and an unsubstituted C2-C19 acyl group.

The halogen atom represented by the above $R^2$ can be a chlorine atom, a bromine atom, and an iodine atom, among which a bromine atom or an iodine atom is preferred.

In a case of a compound having a structure represented by the general formula (6), the halogen atom represented by $R^2$ is preferably a bromine atom or a chlorine atom, and especially preferably a chlorine atom.

For the above $R^1$, an ester group is the one having the above-described substituted or unsubstituted C1-C18 alkyl group or substituted or unsubstituted aryl group.

Specific examples of the "unsubstituted C1-C18 alkyl group" for the above $R^1$ include the followings; namely, linear saturated alkyl groups such as methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, and n-octadecyl; branched saturated alkyl groups such as i-propyl, i-butyl, s-butyl, and t-butyl; cyclic saturated alkyl groups such as cyclopropyl and cyclobutyl; unsaturated alkyl groups such as 1-propenyl, 2-propenyl, 1-butenyl, 2-butenyl, 3-butenyl, 1-propynyl, 2-propynyl, 1-butynyl, 2-butynyl, and 3-butynyl. Among the above alkyl groups, linear C1-C18 alkyl groups are preferred, and linear C5-C12 alkyl groups are more preferred.

The "unsubstituted aryl group" for the above $R^1$ can be C6-C20 aromatic hydrocarbon groups such as phenyl, naphthyl, anthryl, phenanthryl, and pyrenyl; and condensed aromatic cyclic groups such as anthraquinolyl and benzopyrenyl. The number of aryl groups can be one or two as in carbazolyl.

The unsubstituted aryl groups as described above can be further condensed with another aromatic ring selected from benzene, naphthalene, anthracene, phenanthrene, pyrene, furan, pyrrole, thiophene, pyridine, and the like. Specific examples include compounds in which an aryl group is condensed with a 5- or 6-membered heterocyclic group such as carbazolyl, quinolyl, isoquinolyl, indolenyl, benzothienyl, and benzofuryl. The unsubstituted aryl group is preferably phenyl, naphthyl, anthracenyl, carbazolyl, and benzothienyl, and especially preferably phenyl.

For the above $R^1$, the "unsubstituted heteroaryl group" can be C5-C6 aromatic heterocyclic groups having one or two nitrogen atom(s), oxygen atom(s), or sulfur atom(s) such as pyridyl, pyradyl, pyrimidyl, pyrrolyl, imidazolyl, thienyl, furyl, and pyradyl; and C5-C13 aromatic heterocyclic groups in which an aryl group is condensed with a 5- or 6-membered heterocyclic group such as quinolyl, isoquinolyl, indolenyl, benzothienyl, and benzofuryl. The unsubstituted heteroaryl group is preferably pyrrolyl, pyridyl, thienyl, indolyl, and benzothienyl.

For the above $R^1$, the "unsubstituted C1-C18 alkoxyl group" is alkoxyl groups having the above-described unsubstituted C1-C18 alkyl group. Alkoxyl groups having the above-described preferable alkyl group are similarly preferred.

Preferable specific examples thereof include linear C1-C18 alkoxyl groups such as methoxy, ethoxy, n-propoxy, n-butoxy, n-pentyloxy, n-hexyloxy, n-heptyloxy, n-octyloxy, n-nonyloxy, n-decyloxy, n-undecyloxy, n-dodecyloxy, n-tridecyloxy, n-tetradecyloxy, n-pentadecyloxy, n-hexadecyloxy, n-heptadecyloxy, and n-octadecyloxy. More preferable specific examples thereof include linear C5-C18 alkoxyl groups such as n-pentyloxy, n-hexyloxy, n-heptyloxy, n-octyloxy, n-nonyloxy, n-decyloxy, n-undecyloxy, and n-dodecyloxy.

For the above $R^1$, the "substituted amino group" represents an amino group substituted with one or two of the above-described "unsubstituted C1-C18 alkyl group" or the above-described "unsubstituted aryl group", each independently. Preferable unsubstituted C1-C18 alkyl groups and unsubstituted aryl groups are each the same as defined above.

As the number of substituent groups, two is preferred over one. In terms of a manner of substitution, a substitution with two of the above-described alkyl group or the above-described aryl group is preferred over a substitution with each one of the alkyl group and the aryl group. A dialkyl-substituted amino group is more preferred, while an unsubstituted amino group is even more preferred. The substituent group in the substituted amino group, namely an unsubstituted C1-C18 alkyl group and an unsubstituted aryl group, can further have a substituent group as will be described below.

For the above $R^1$, the "C1-C18 alkyl group substituted with a silyl group" is the one in which any site of the above-described C1-C18 alkyl group is substituted with a silyl group. A silicon atom of the silyl group is directly bonded to a carbon atom of the alkyl group. While no limitation is imposed on the silyl group, it can be a silyl group substituted with three C1-C8 alkyl groups or aryl groups, each independently. Specific examples thereof include trimethyl silyl, triethyl silyl, triisopropyl silyl, triphenyl silyl, t-butyldimethyl silyl, and t-butyldiphenyl silyl. Among these examples, a preferable silyl group can be the silyl group substituted with three C1-C3 alkyl groups.

For the above $R^1$, the "unsubstituted C2-C19 acyl group" is an acyl group having the above-described "unsubstituted C1-C18 alkyl group" or the above-described "unsubstituted aryl group." The structural formula thereof is expressed as "—C(O)-(unsubstituted C1-C18 alkyl group)" or "—C(O)-(unsubstituted aryl group)", respectively. At this point, "C(O)" represents that the carbon atom and the oxygen atom are connected by a double bond; namely, a carbonyl group. Preferable unsubstituted C1-C18 alkyl groups and unsubstituted aryl groups are each the same as defined above. Especially preferably, the acyl group is an acetyl group.

For the above $R^1$, the substituent group in the "substituted C1-C18 alkyl group", the "substituted aryl group", the "substituted heteroaryl group", the "substituted C1-C18 alkoxyl group", the "substituted C2-C19 acyl group", and the substituent group in the case of "the substituent group in the substituted amino group further have a substituent group" is independently selected from the group consisting of a halogen atom, a hydroxyl group, a cyano group, a nitro group, a carboxyl group, a formyl group, an ester group, a substituted or unsubstituted C1-C18 alkyl group, a substituted or unsubstituted aryl group, a substituted or unsubstituted heteroaryl group, a substituted or unsubstituted C1-C18 alkoxyl group, a substituted or unsubstituted amino group, a C1-C18 alkyl group substituted with a silyl group, or a substituted or unsubstituted C2-C19 acyl group. No particular limitation is imposed on the number of the substituent groups; however, it is normally one to three, preferably two, and more preferably one. The halogen atom, the ester group, the substituted or unsubstituted C1-C18 alkyl group, the substituted or unsubstituted aryl group, the substituted or unsubstituted heteroaryl group, the substituted or unsubstituted C1-C18 alkoxyl group, the substituted or unsubstituted amino group, the C1-C18 alkyl group substituted with a silyl group, or the substituted or unsubstituted C2-C19 acyl group of the substituent groups are the same as those described for the above $R^1$, and preferable and more preferable examples thereof and the like are also the same as the ones described above.

Among the above substituent groups, a halogen atom, a cyano group, a nitro group, an ester group, a substituted or unsubstituted C1-C18 alkyl group, a substituted or unsubstituted aryl group, a substituted or unsubstituted C1-C18 alkoxyl group, and a substituted or unsubstituted C2-C19 acyl group are preferred, among which a halogen atom, a cyano group, a nitro group, an ester group, an unsubstituted C1-C18 alkyl group, an unsubstituted aryl group, an unsubstituted C1-C18 alkoxyl group, and an unsubstituted C2-C19 acyl group are preferred. Among them, an unsubstituted C1-C18 alkyl group is particularly preferred.

The compound represented by the above formula (1), for example, 1-bromo-2-ethinylbenzene and (2-bromophenyl)ethinyltrimethylsilane are easily obtainable as commercial products. Also, α-bromo-ethinylbenzen is generally synthesized by a method such as Sonogashira reaction of a commercially available 2-bromo-1-iodobenzen and an acetylene derivative following a publicly known method disclosed in literature such as NON-PATENT DOCUMENTS 1 to 4.

Specific examples of the compound represented by the above formula (1) include, for example, Compounds 1 to 15 as shown below. Unless otherwise specifically stated, a blank column represents a hydrogen atom, Me represents a methyl group, and Ph represents a phenyl group in Table 1.

TABLE 1

|  |  | R³¹ | | | |
|---|---|---|---|---|---|
| R³² | | | R² | | |
| R³³ | | | | | |
| | R³⁴ | | R¹ | | |

| Compound No. | R¹ | R² | R³¹ | R³² | R³³ | R³⁴ |
|---|---|---|---|---|---|---|
| 1 | H | I | | | | |
| 2 | CN | I | | Me | | Me |
| 3 | CH₃ | Br | | | | Me |
| 4 | C₁₀H₂₁ | Br | | Br | | |
| 5 | NH₂ | Br | | | NO₂ | |
| 6 | OMe | Br | | CO₂Me | | |
| 7 | SiMe₃ | Br | | | | |
| 8 | COMe | Br | | | | |
| 9 | Ph | Br | | | | |
| 10 | 2-Me-Ph | Br | | | | |

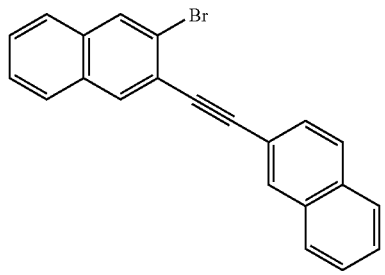

11

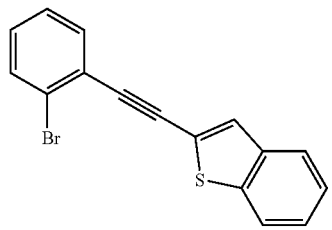

12

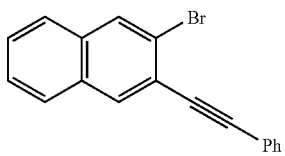

13

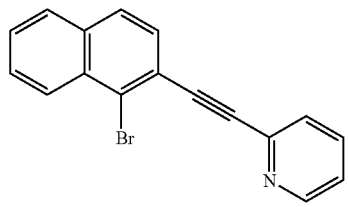

14

TABLE 1-continued

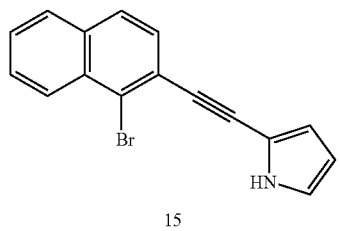 [SMILES: Brc1c(C#Cc2ccc[nH]2)ccc2ccccc12]

15

The compound represented by the above formula (1) includes the compounds represented by the above formulas (3) to (6). While any of them is preferred, the compounds represented by the formulas (3) and (6) are especially preferred.

Specific examples of the compounds represented by formulas (3) to (6) are sequentially shown below; however, the present invention is not limited thereto. Specific examples of Compounds 16 to 25 represented by the above formula (3) are now shown below.

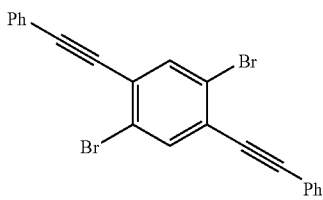

16

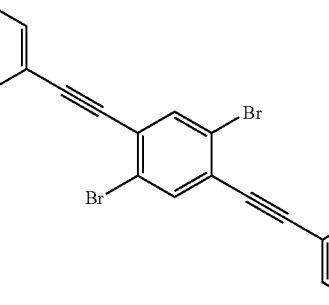

17

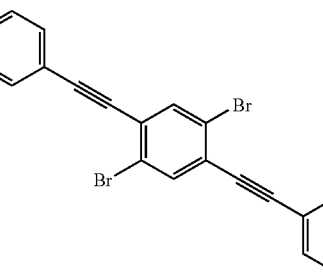

18

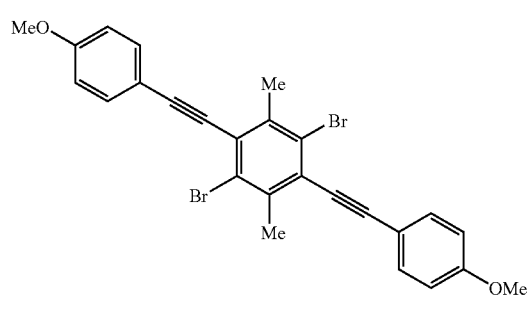
19
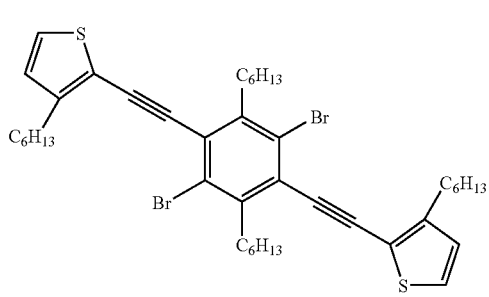
24
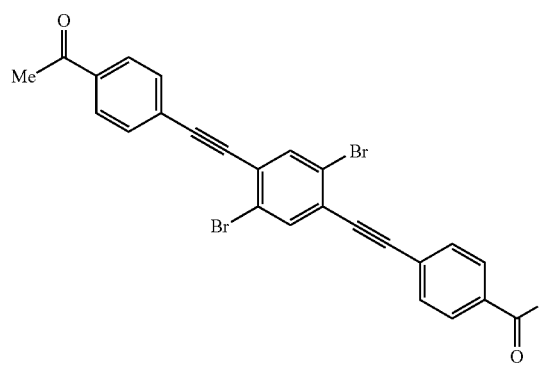
20
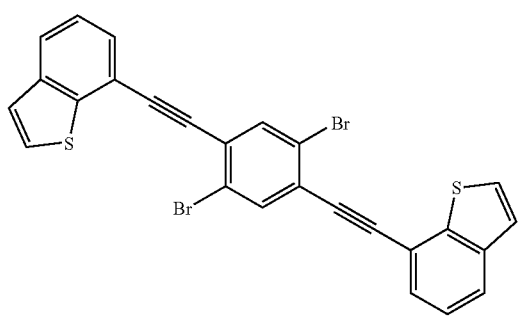
25
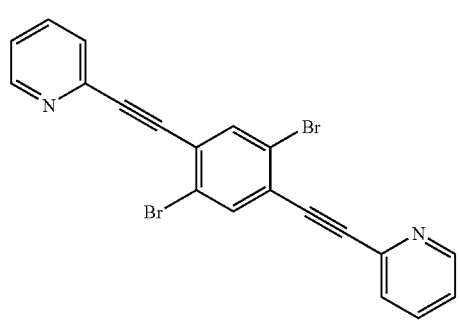
21
Compounds 26 to 35 are subsequently shown as specific examples of the compound represented by the above formula (4).
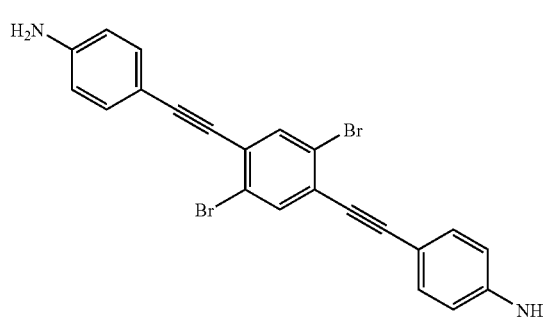
22
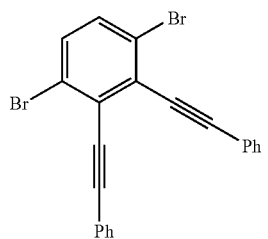
26
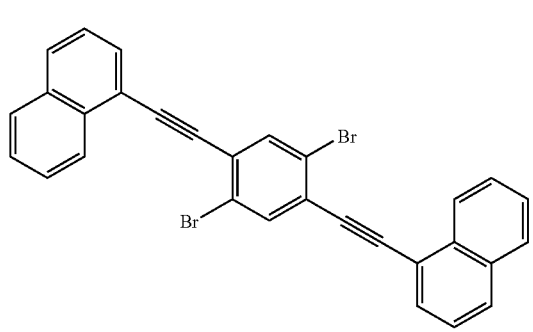
23
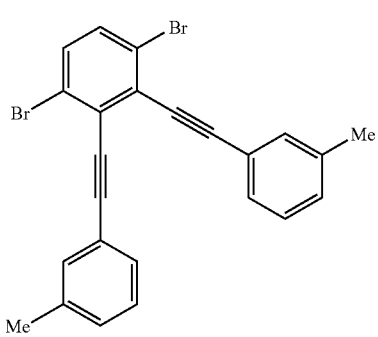
27

28
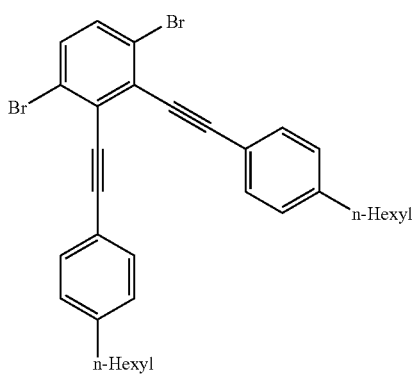
29
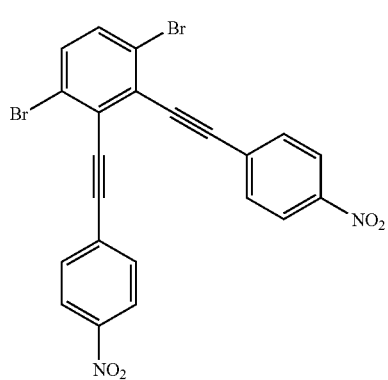
30
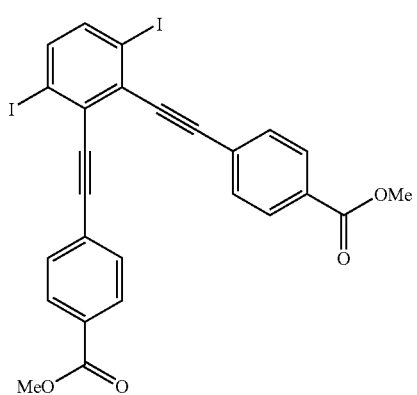
31
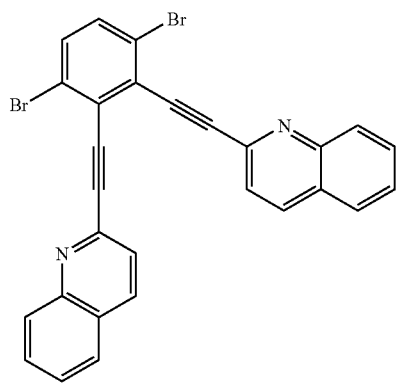
32
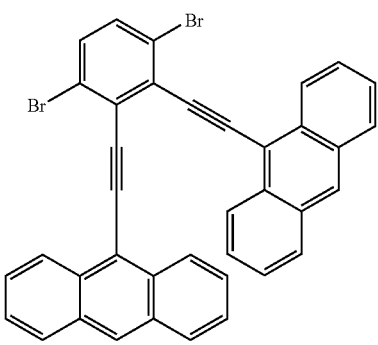
33
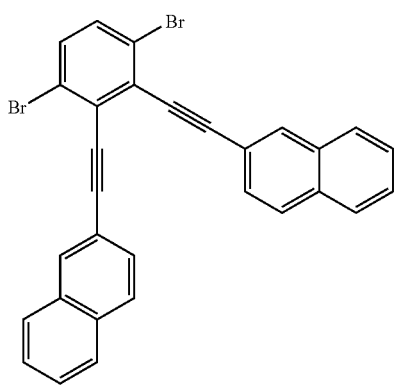
34
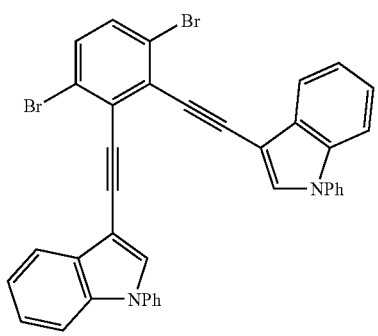
35
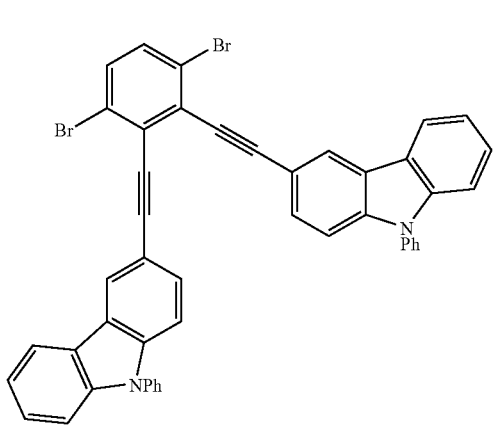
Compounds 36 to 45 are further shown as specific examples of the compound represented by the above formula (5).

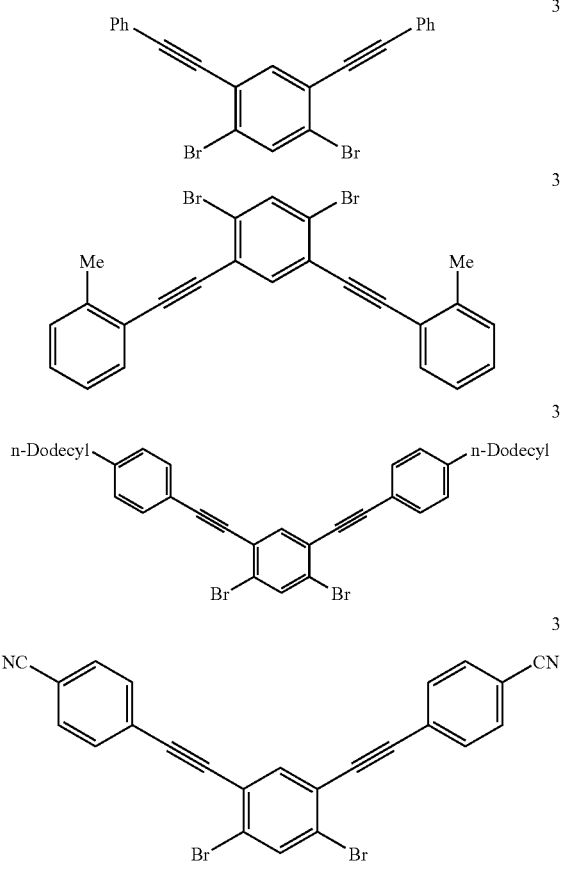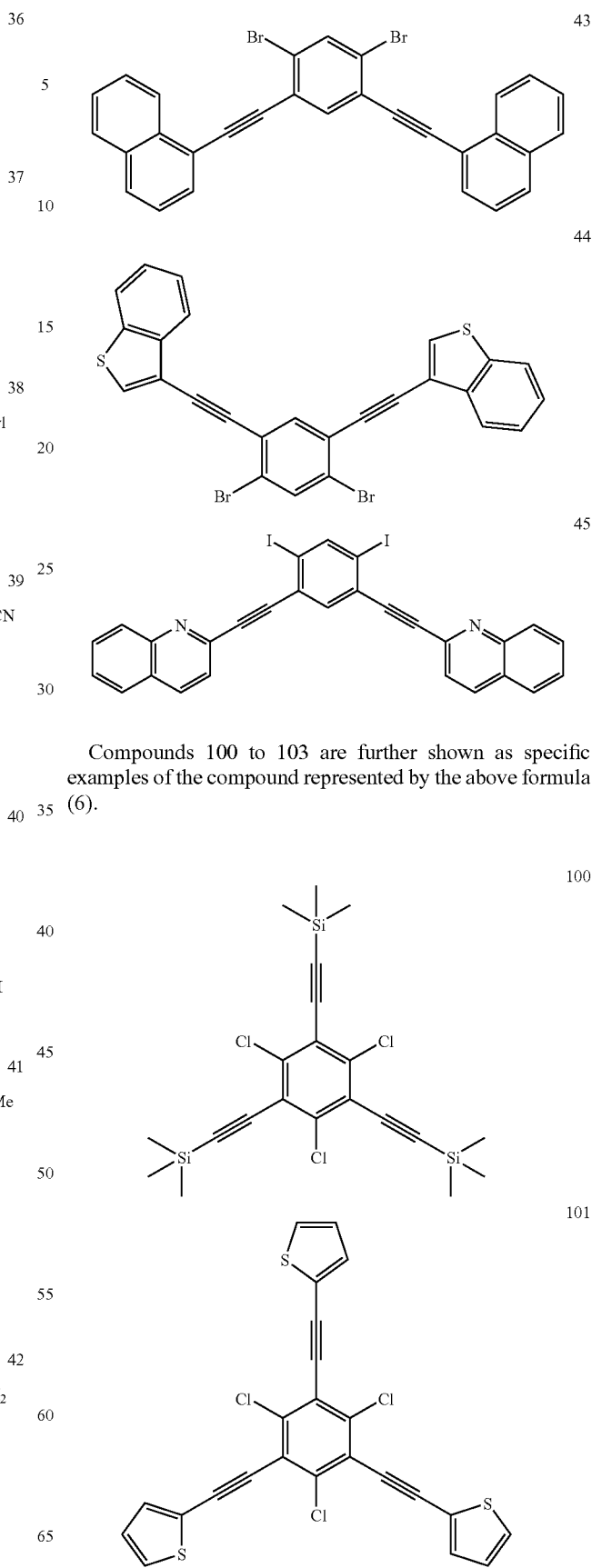
Compounds 100 to 103 are further shown as specific examples of the compound represented by the above formula (6).

-continued

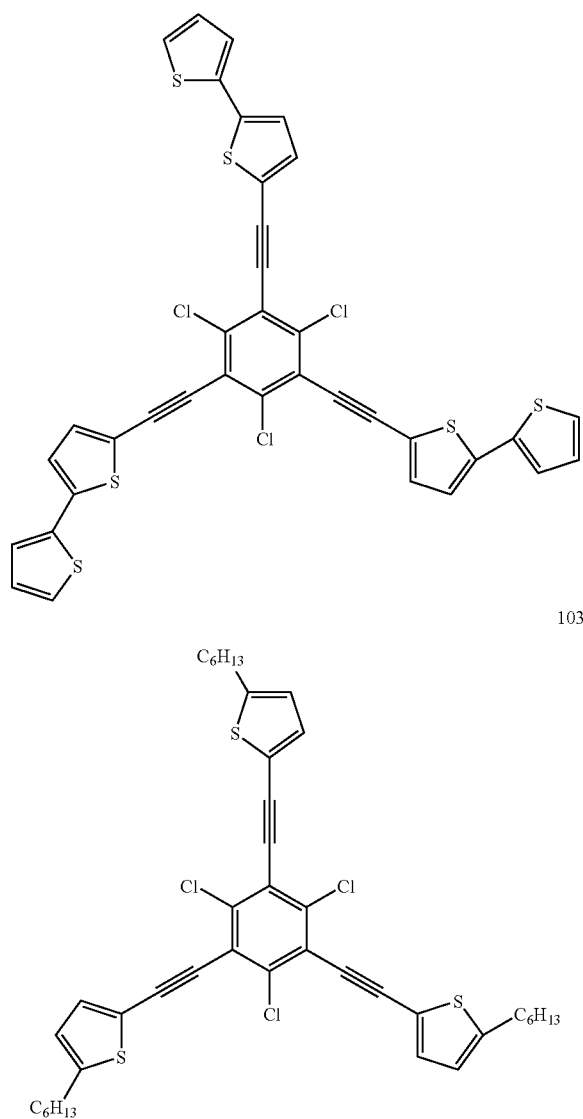

The above sulfur compound can be at least one kind selected from the group consisting of sulfur, hydrogen sulfide, metal hydrosulfide, and metal sulfide. These substances can be employed singly or a plurality of them can be employed in combination. The above metal hydrosulfide can be a hydrous and/or an anhydrous alkaline metal hydrosulfide, and sodium hydrosulfide and potassium hydrosulfide are preferred as specific examples thereof. The above metal sulfide can be a hydrous and/or an anhydrous alkaline metal hydrosulfide, and a transition metal hydrosulfide, and the like. Specific examples thereof include sodium sulfide, potassium sulfide, iron sulfide, and copper sulfide.

As the above sulfur compound, sulfur, a hydrous and/or an anhydrous sodium hydrosulfide, and a hydrous and/or an anhydrous sodium sulfide are preferred, among which a hydrous sodium hydrosulfide and a hydrous sodium sulfide are more preferred.

The above selenium compound can be metallic selenium, NaSeH, KSeH, and selenium oxide. Among them, metallic selenium and NaSeH are preferred, among which metallic selenium is more preferred.

In a method for producing the compound of the above formula (2), a sulfur compound or a selenium compound employed in a reaction is used at a ratio of normally 1 to 16 moles, preferably 2 to 8 moles, and more preferably 2 to 5 moles, to 1 mole of the compound of the above formula (1).

A reaction solvent can be either used or not used. Normally, when the compound represented by the above formula (1) is solid, it is better to use a reaction solvent. While it is possible to carry out a reaction without a solvent in a case where the compound is liquid, it is preferable to employ at least one solvent having a boiling point of 100° C. or higher in a reaction mixture according to the production method the present invention. It is preferable because by doing so a reaction rate of the reaction for producing the compound represented by the above formula (2) is improved.

As a solvent having a boiling point of 100° C. or higher, amide such as N-methyl-2-pyrrolidone, N,N-dimethylformamide, and N,N-dimethylacetamide; glycol such as ethylene glycol, propylene glycol, and polyethylene glycol; and sulfoxide such as dimethyl sulfoxide are preferred, among which N-methyl-2-pyrrolidone, N,N-dimethylformamide, and N,N-dimethylacetamide are more preferred.

The solvent having a boiling point of 100° C. or higher is better to be used at a ratio of 0.01 to 100 moles, preferably 0.1 to 80 moles, and more preferably 20 to 50 moles, to 1 mole of the compound of the above formula (1).

It is better to carry out a reaction at reaction temperature of −50° C. to 300° C. in the above-described production method. The reaction temperature can be changed as needed within the above temperature range. It is preferably −10° C. to 250° C., and more preferably 40° C. to 200° C.

It is not mandatory to add a catalyst to a reaction for synthesizing the compound represented by the above formula (2); however, there is a case in which the reaction proceeds smoothly when a catalyst is used. It is better to use a catalyst in a case when the reaction does not proceed smoothly.

As a metal catalyst to be used, a copper atom and metal halide, particularly copper halide such as copper(I) chloride, copper(II) chloride, copper(I) bromide, copper(II) bromide, copper(I) iodide, and copper(II) iodide are preferred, among which a copper atom, copper(I) bromide, and copper(I) iodide are more preferred.

The amount of the above catalyst to be used is 0.01 to 1 mole, preferably 0.1 to 0.5 mole, and more preferably 0.1 to 0.2 mole, with respect to 1 mole of the compound of the above formula (1).

While the reaction time is normally one hour to 50 hours, it is preferable to adjust the reaction temperature, the amount of the halogenating agent and the sulfur compound or the selenium compound so that the reaction completes roughly within 24 hours.

A target compound can be isolated and purified from the reaction mixture as needed following a publicly known method. It is possible to carry out purification by sublimation, especially purification by vacuum sublimation, to obtain a target compound of high purity.

$R^1$, $R^3$, and n in the compound represented by the above formula (2) have the same meanings as in the above formula (1), and other parameters such as preferable groups are also the same as those described for the above formula (1). X represents a sulfur atom or a selenium atom, both of which are preferred.

Compounds 46 to 92 and 104 to 107 are illustrated below as specific examples of the compound represented by the above formula (2); however, the compound is not limited thereto. It is burdensome to list the compounds represented by the formula (2) in which X is either a sulfur atom or a selenium atom separately from the ones in which X is the other atom. Therefore, when $R^1$ and $R^3$ are identical, only the ones represented by the above formula (2) in which X is a sulfur atom are illustrated as Compounds 46 to 92 in the present specification as a matter of convenience. It is to be noted that the sulfur atom can be alternatively read as the selenium atom in the compounds 46 to 92.
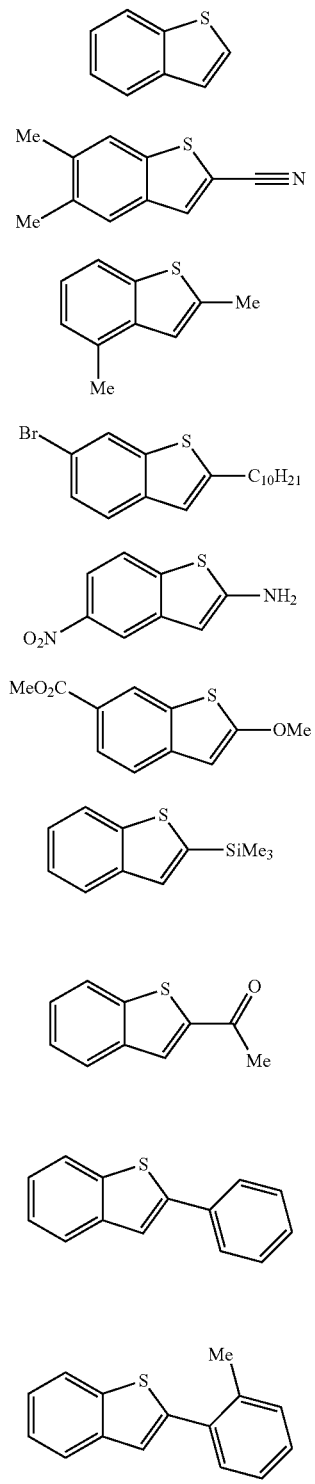
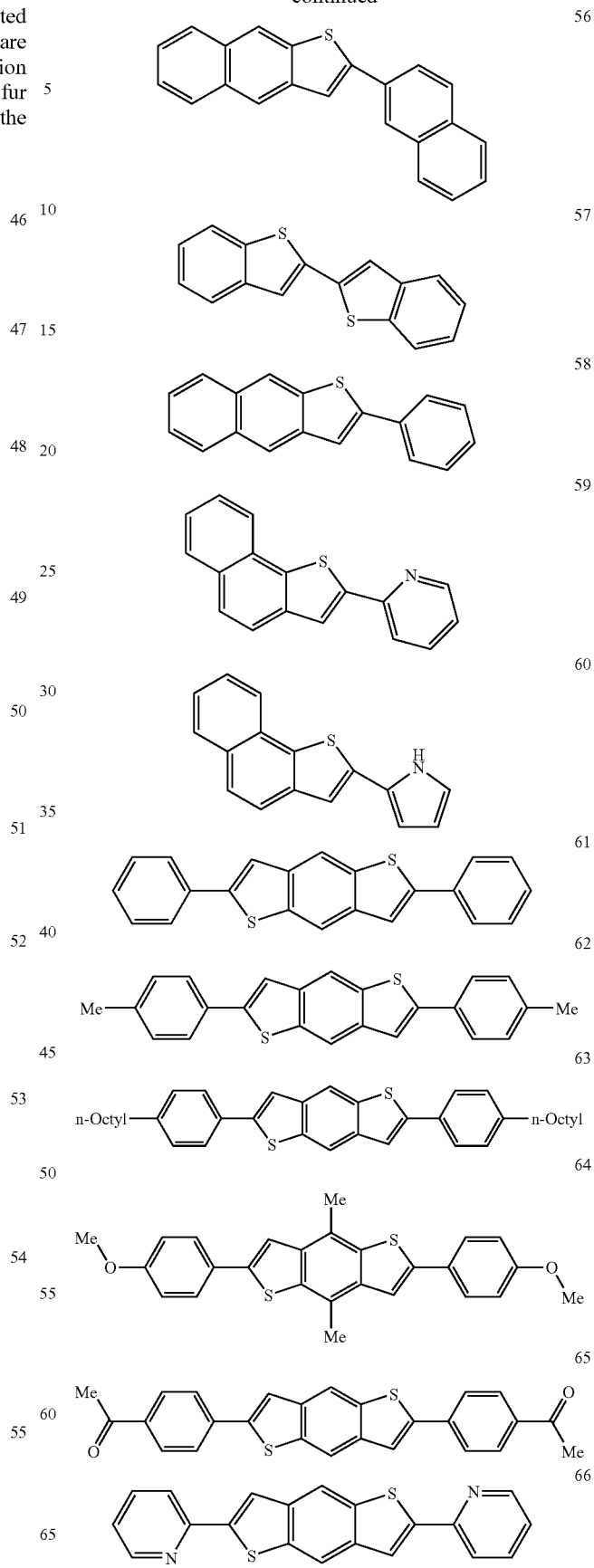

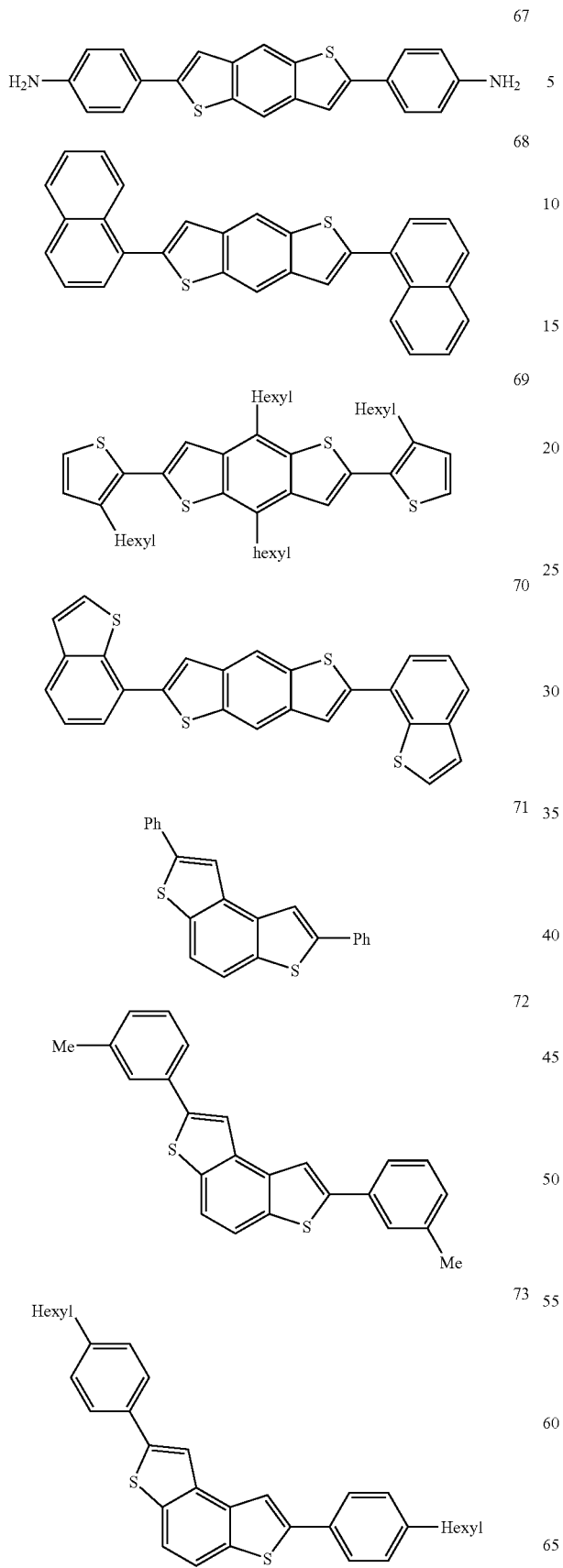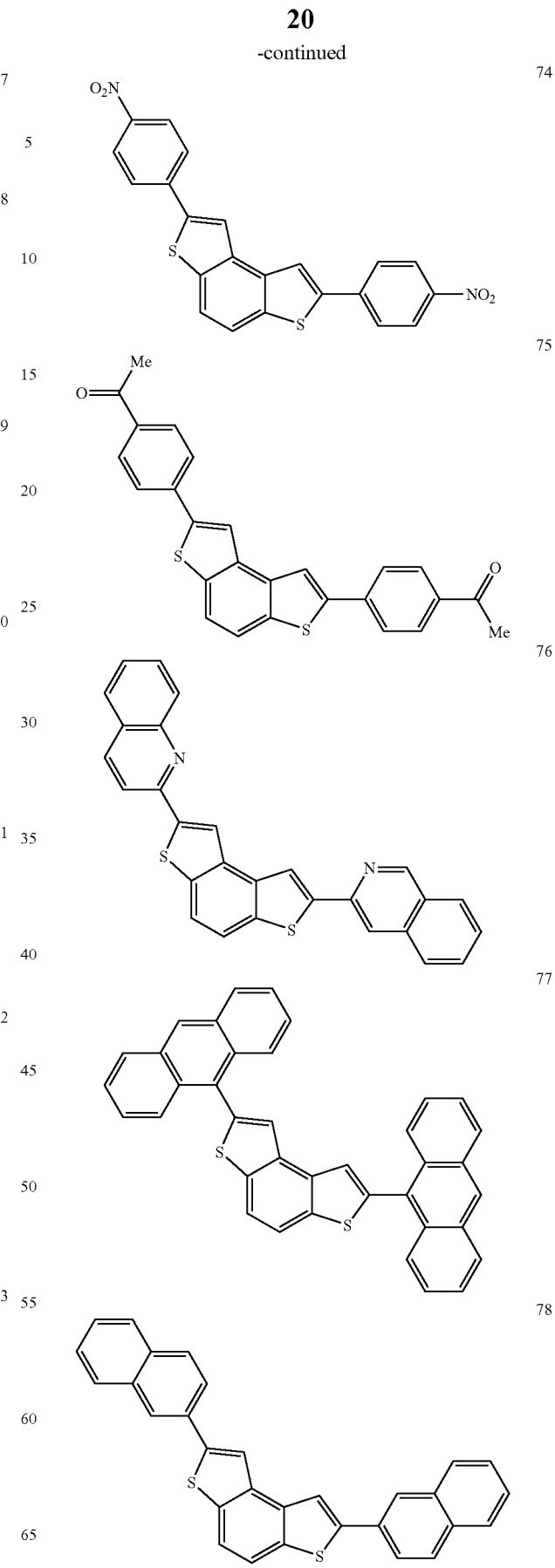

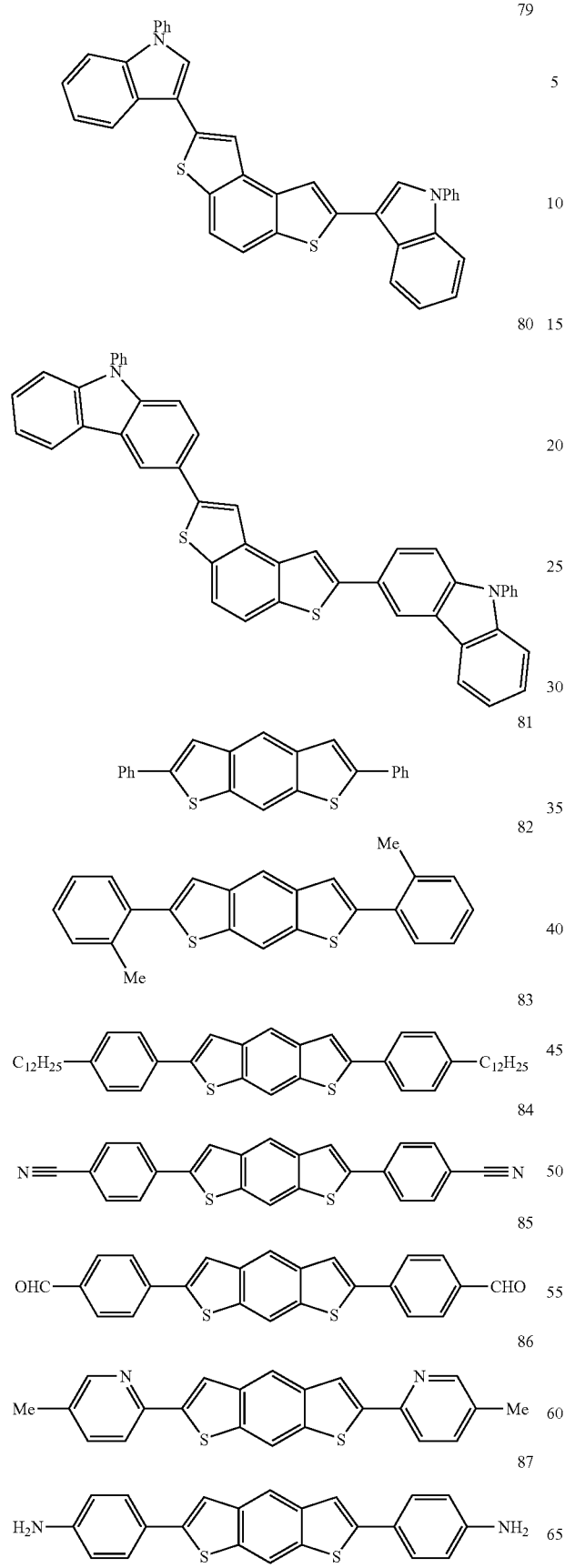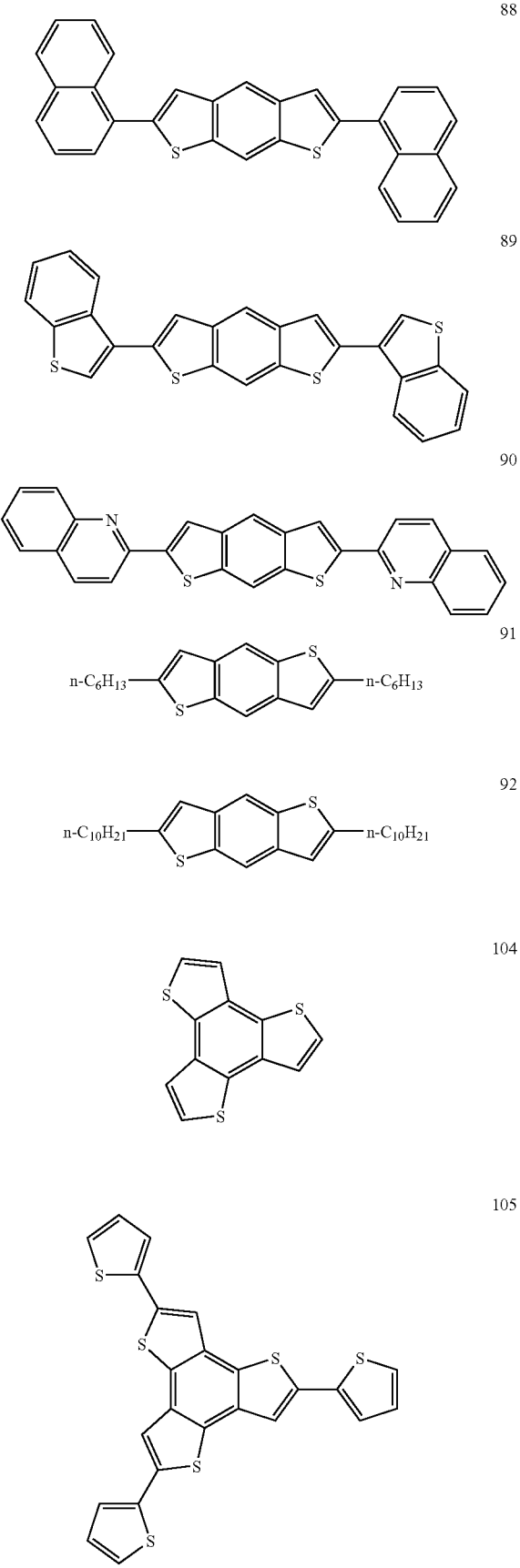

-continued

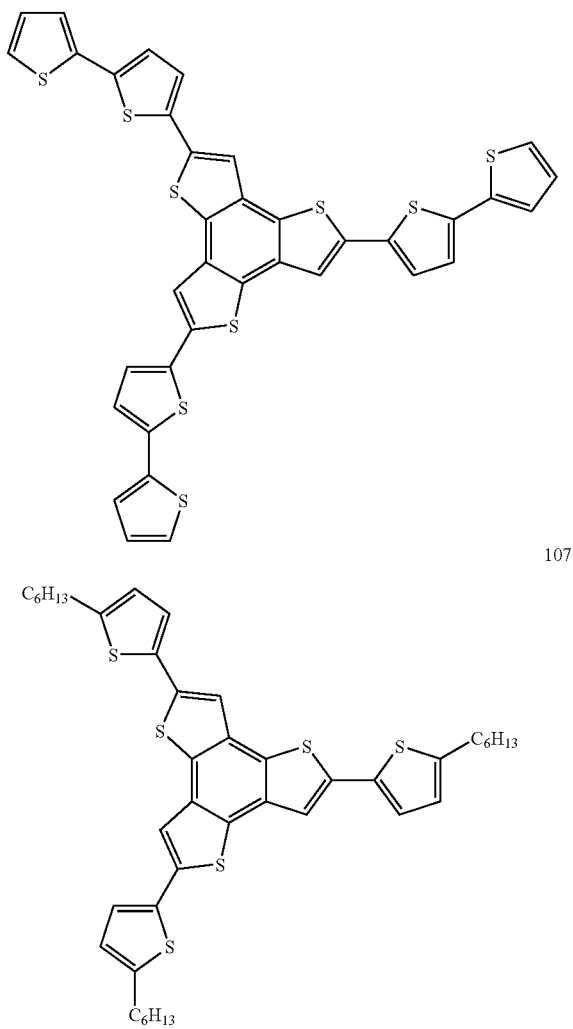

Examples

The present invention is described further in detail hereinbelow with Examples; however, the present invention is not limited thereto.

A structure of the target compound is determined by 1H NMR (i.e., 1H nuclear magnetic resonance spectrometry), MS (i.e., mass spectrometry), melting point measurement, and elementary analysis, as needed. The following instruments were used;

1H NMR: JEOL Lambda 400 spectrometer
MS: Shimadzu QP-5050A
Melting point measurement: Yanagimoto micromelting point apparatus MP-S3
Elementary analysis: Parkin Elmer 2400 CHN elemental analyzer Example 1

2,6-diphenylbenzo[1,2-b:4,5-b']dithiophene (Compound 61)

To an NMP (N-methyl-2-pyrrolidone, 30 ml) solution containing 1,4-dibromo-2,5-bisphenylbenzene (Compound 16) (6.54 g, 15 mmol), 70% $NaSH \cdot nH_2O$ (3.60 g, 92 mmol) and copper iodide (0.14 g, 0.8 mmol) were added, and the resulting mixture was left for 3 hours, while the inside temperature was kept at 140° C. to 150° C. The mixture was then cooled and toluene (100 ml) was added. Precipitated solid was separated by filtration and washed with toluene (30 ml) and methanol (30 ml), followed by drying. The obtained compound was purified by sublimation, thereby the Compound 61 was obtained (4.37 g, yield: 85%).

MS (70 eV, EI) m/z=342 (M+)

Example 2

2,6-diphenylbenzo[1,2-b:4,5-b']diselenophen (Compound 61, S=Se)

Under nitrogen atmosphere, selenium (98.7 mg, 1.25 mmol) and $NaBH_4$ (47.3 mg, 1.25 mmol) were dissolved in ethanol (5 ml). The resulting mixture was stirred for 30 minutes, while it was kept at 5° C. Then, 1,4-dibromo-2,5-bisphenylbenzene (Compound 16) (216 mg, 0.50 mmol) and NMP (12 ml) were added to the mixture, followed by heating at the inside temperature of 190° C. for 20 hours. The reaction liquid was poured into water and precipitated solid was separated by filtration. The solid thus obtained was washed with methanol (30 ml) and acetone (30 ml), and dried. The obtained compound was purified by sublimation, thereby a yellow crystalline compound was obtained (Compound 61, S=Se) (114 mg, yield: 52%).

MS (70 eV, EI) m/z=436 (M+)

Synthetic Example 1

1,4-dibromo-2,5-bis(octyne-1-yl)benzene ($Br_2C_6H_4$ ($-C{\equiv}C-CH_2CH_2CH_2CH_2CH_2CH_3)_2$)

Under nitrogen atmosphere, 1,4-dibromo-2,5-diiodobenzene (3.0 g, 6.2 mmol) was dissolved in diisopropylamine (45 ml) and anhydrous benzene (45 ml), followed by stirring for 30 minutes. Copper iodide (235 mg, 0.12 mmol), $PdCl_2(PPh_3)_2$ (430 mg, 0.61 mmol), and 1-dodecene (1.9 ml, 12.9 mmol) were added to the mixture, followed by stirring at room temperature for 14 hours. The reaction liquid was poured into water and extracted with chloroform, and the obtained organic layer was washed with 200 ml of water three times. The resulting organic layer was dried over anhydrous sodium sulfate and purified by a column chromatography (silica gel and methylene chloride:hexane=1:3), followed by recrystallization in ethanol, thereby colorless powdery 1,4-dibromo-2,5-bis(octyne-1-yl)benzene was obtained (1.56 g, yield: 56%).

1H-NMR (400 MHz, CDCL3) δ7.59 (s, 2H) 2.45 (t, J=7.2 Hz, 4H) 1.65-1.23 (m, 32H) 0.88 (t, J=6.4 Hz, 6H)

Example 3

2,6-didecylbenzo[1,2-b:4,5-b']dithiophene (Compound 91)

Under nitrogen atmosphere, 1,4-dibromo-2,5-bis(octyne-1-yl)benzene (216 mg, 0.5 mmol) and 70% $NaSH \cdot nH_2O$ (96 mg) were dissolved in NMP (12 ml), followed by heating at the inside temperature of 160° C. to 170° C. for 20 hours. Upon completion of the reaction, the solution was poured in water and stirred for one hour, followed by extraction with 15 ml of hexane three times. The obtained organic layer was washed with 100 ml of saturated saline three times, and dried over anhydrous sodium sulfate and then concentrated, thereby 2,6-didecylbenzo[1,2-b:4,5-b']dithiophene was obtained (Compound 91) (77.1 mg, yield: 43%).

1H-NMR (400 MHz, CDCl$_3$) δ8.01 (s, 2H) 6.98 (s, 2H) 2.89 (t, J=7.2 Hz, 4H) 1.75-1.26 (m, 32H) 0.88 (t, J=6.4 Hz, 6H)

MS (70 eV, EI) m/z=470 (M+)

m.p. 144.5-145.5° C.

Examples 4 to 8

Compounds 16 to 61 as shown above were synthesized in a similar way as in Example 1, except substituting each of the sulfur compound, the amount of sulfur compound used, the reaction temperature, the reaction time, and the catalyst for the ones in Table 2 as shown below.

Comparative Examples 1 to 3

Compounds 16 to 61 as shown above were synthesized for comparison according to the method described in "General Procedure" in Examples 2a-f, 4a-c, and g in the NON-PATENT DOCUMENT 1, except substituting each of the sulfur compound, the amount of sulfur compound used, the reaction temperature, the reaction time, and the catalyst for the ones in Table 2 as shown below.

TABLE 2

| | Sulfur compound, Amount (molar fold) | Solvent, Reaction temperature, Reaction time (hours) | Catalyst, Amount (molar fold) | Yield (%) |
|---|---|---|---|---|
| Comparative Example 1 | Na$_2$S•5H$_2$O, 3 | EtOH, reflux 8 | None | 0 |
| Comparative Example 2 | Na$_2$S•5H$_2$O, 3 | EtOH, reflux 8 | CuI 0.05 | 0 |
| Comparative Example 3 | NaSH•xH$_2$O (70%), 3 | EtOH, reflux 8 | CuI 0.05 | 0 |
| Example 4 | NaSH•xH$_2$O (70%), 3 | NMP, 85° C. 8 | CuI 0.05 | 50.0 |
| Example 5 | NaSH•xH$_2$O (70%), 3 | NMP, 140° C. 8 | None | 78.8 |
| Example 6 | NaSH•xH$_2$O (70%), 3 | NMP, 140° C. 8 | CuI 0.05 | 87.1 |
| Example 7 | Na$_2$S•5H$_2$O, 3 | NMP, 140° C. 8 | None | 83.2 |
| Example 8 | Na$_2$S•5H$_2$O, 3 | NMP, 140° C. 8 | CuI 0.05 | 76.5 |

In Comparative Example 1, the reaction was carried out using sodium sulfide in ethanol solvent according to the method described in "General Procedure" in Examples 2a-f, 4a-c, and g in the NON-PATENT DOCUMENT 1. The reaction was hardly found to proceed in this method. In Comparative Example 2, copper iodide was added as a catalyst to the reaction system of the Comparative Example 1; however, the reaction was not found to proceed. In Comparative Example 3, the reaction was carried out by substituting hydrous 70% sodium hydrosulfide for the sulfur source in Comparative Example 1; however, the reaction was not found to proceed.

In Example 4, the reaction was carried out at reaction temperature almost close to the boiling point of ethanol using NMP, which was amide. NMP is a high-boiling solvent having a boiling point of 100° C. or higher. As a result, the target Compound 61 was successfully obtained with a yield of 50%.

Furthermore, experiments of Examples 5 to 8 were carried out using systems in which the catalyst was copper iodide and the solvent was NMP. As a result, notably, the target Compound 61 was obtained with a yield of as high as about 80%. It was understood that the method of the present invention was superior as exemplified by that a compound which could not have been synthesized by a conventional method was easily produced as shown above.

NON-PATENT DOCUMENTS 3 and 4 disclose a popularly used conventional method for synthesizing [1]benzochalcogeno[3,2-b][1]benzochalcogenophene, namely, a method for synthesizing the above compound by applying tert-butyllithium to bis(2-bromophenyl)acetylene in THF at low temperature, followed by addition of sulfur, metallic selenium, or metallic tellurium. The following experiments were carried out as shown in Comparative Example 4 and Example 9 to compare the above conventional method and the present invention.

Synthetic Example 2

1,4-dibromo-2,5-bis(dodecen-1-yl)benzene
(Br$_2$C$_6$H$_4$(—C≡C-n-C$_{10}$C$_{10}$H$_{21}$)$_2$)

Starting from 1,4-dibromo-2,5-diiodobenzene (5.0 g, 10.3 mmol), colorless powdery 1,4-dibromo-2,5-bis(dodecen-1-yl)benzene (4.30 g, yield: 75%) was obtained according to the method described in Synthetic Example 1 using corresponding acetylene.

MS (70 eV, EI) m/z=564 (M+)

Comparative Example 4

2,6-didodecylbenzo[1,2-b:4,5-b']dithiophene
(Compound 92)

Under nitrogen atmosphere, 1,4-dibromo-2,5-bis(dodecen-1-yl)benzene (1.0 g, 1.77 mmol) was dissolved in anhydrous ether (20 ml) and cooled to −78° C., to which 1.59 M solution of t-butyllithium.entane (4.46 ml, 3.9 mmol) was added. The mixture was stirred for 30 minutes at the same temperature, after which the temperature was elevated to −30° C. Sulfur powder (133 mg, 4.25 mmol) was then added, and the temperature was further elevated to room temperature. Anhydrous ethanol (10 ml) was added and the mixture was stirred for three hours. The mixture was then extracted with 15 ml of chloroform three times and washed with 100 ml of water three times, followed by drying over anhydrous sodium sulfate and concentration by using an evaporator. The resulting mixture was purified by a column chromatography (silica gel and methylene chloride:hexane=1:3) and recrystalized in hexane, thereby Compound 92 was obtained (102 mg, yield: 11%).

Example 9

2,6-didodecylbenzo[1,2-b:4,5-b']dithiophene (Compound 92)

Using 1,4-dibromo-2,5-bis(dodecen-1-yl)benzene (1.0 g, 1.77 mmol), the reaction was carried out according to the method of Example 3 and the resulting mixture was purified according to the method of Comparative Example 4, thereby Compound 92 was obtained (398 mg, yield: 43%).

The results obtained from Comparative Example 4 and Example 9 were summarized in Table 3 as follows.

TABLE 3

|  | Sulfur Compound | Solvent & conditions | Yield |
|---|---|---|---|
| Comparative 4 | Sulfur | Diethyl ether, t-BuLi-78° C. | 11% |
| Example 9 | NaSH•xH$_2$O (70%) | NMP, 160-170° C. | 43% |

In Comparative Example 4, which was a conventional method, the yield was as extremely low as 11%, while in Example 9, which was the present invention, the target compound was obtained with a moderate yield of 43%. Also, the present invention was shown to be a superior synthetic method having a greater versatility compared to the conventional method.

Example 10

Benzo[1,2-b:3,4-b':5,6-b"]trithiophene (Compound 104)

Under nitrogen atmosphere, sodium sulfide nonahydrate (1.54 g, 6.42 mmol) was added to anhydrous NMP (40 ml) and the mixture was stirred for ten minutes. To this mixture, 1,3,5-trichloro-2,4,6-tris[(trimethylsilyl)ethinyl]benzene (Compound 100)(500 mg, 1.07 mmol) was added, followed by heating at 185° C. to 195° C. for 12 hours. Upon completion of the reaction, the mixture was poured into water (400 ml) and precipitated solid was collected by filtration. The solid thus obtained was dissolved in chloroform (200 ml), and the resulting solution was washed with saturated saline. The solution was dried over anhydrous magnesium sulfate and the solvent was removed under reduced pressure. Solid thus obtained was purified by a column chromatography (silica gel and hexane), thereby white crystalline Compound 104 was obtained (156 mg, yield: 60%).

$^1$H-NMR (270 MHz, CDCl$_3$) δ7.64 (d, J=5.4 Hz, 3H) 7.54 (d, J=5.4 Hz, 3H), M.S. (70 eV, EI) m/z=246 (M$^+$)

As shown above, a benzochalcogenophene derivative can be simply and efficiently produced according to the present invention. Therefore, the method for producing an aromatic compound of the present invention, namely, the method for producing a benzochalcogenophene derivative, is extremely useful.

INDUSTRIAL APPLICABILITY

The method for producing an aromatic compound of the present invention enables simple and efficient production of a benzochalcogenophene derivative; therefore, it can be applied in various industrial fields.

The invention claimed is:

1. A compound represented by the formula (3'-2):

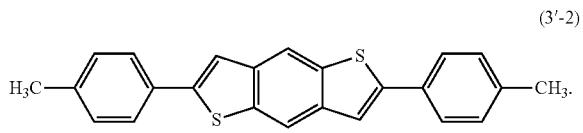 [SMILES: Cc1ccc(-c2cc3cc4sc(-c5ccc(C)cc5)cc4cc3s2)cc1]

(3'-2)

* * * * *